(12) United States Patent
Combs

(10) Patent No.: US 6,363,272 B1
(45) Date of Patent: Mar. 26, 2002

(54) CONNECTOR FOR FETAL PROBE

(75) Inventor: Stephen Combs, East Haven, CT (US)

(73) Assignee: GE Medical Systems Information Technologies, Inc., Waukesha, WI (US)

(*) Notice: Subject to any disclaimer, the term of this patent is extended or adjusted under 35 U.S.C. 154(b) by 0 days.

(21) Appl. No.: 09/679,318

(22) Filed: Oct. 4, 2000

Related U.S. Application Data

(62) Division of application No. 09/237,468, filed on Jan. 26, 1999, now Pat. No. 6,151,520.

(51) Int. Cl.[7] ............................................. A61B 5/0448
(52) U.S. Cl. ..................... 600/376; 600/511; 439/668; 439/675; 439/852; 439/909
(58) Field of Search ..................... 600/376, 394, 600/511; 606/32; 607/149, 152; 439/852, 909, 668, 675

(56) References Cited

U.S. PATENT DOCUMENTS

| 3,750,094 A | * | 7/1973 | Zenkich ...................... 600/394 |
| 3,827,428 A | | 8/1974 | Hon et al. |
| 3,910,271 A | | 10/1975 | Neward |
| RE28,990 E | | 10/1976 | Hon et al. |
| 4,671,591 A | * | 6/1987 | Archer ........................ 600/394 |
| 5,168,876 A | | 12/1992 | Quedens et al. |
| 5,199,432 A | | 4/1993 | Quedens et al. |
| 5,205,288 A | | 4/1993 | Quedens et al. |
| 5,257,622 A | | 11/1993 | Hopper et al. |
| 5,373,843 A | | 12/1994 | Quedens et al. |
| 5,377,677 A | | 1/1995 | Dowd et al. |
| 5,388,579 A | | 2/1995 | Dowd et al. |
| 5,404,876 A | | 4/1995 | DiSabito et al. |
| 5,615,674 A | | 4/1997 | Maurer |
| 5,662,103 A | | 9/1997 | Smith et al. |
| 5,665,477 A | | 9/1997 | Meathrel et al. |
| 5,671,736 A | | 9/1997 | Pettit et al. |
| 5,680,859 A | | 10/1997 | Urion et al. |

* cited by examiner

Primary Examiner—Lee Cohen
(74) Attorney, Agent, or Firm—Michael Best & Friedrich LLP

(57) ABSTRACT

A fetal electrode assembly including a housing having a first opening for receiving a first connector and a second opening for receiving a second connector. The second connector is a snap connector of an electrode mounted on a mother's body. A support is disposed within the housing and has an access opening communicating with the second opening. A contact is mounted on the support opposite the second opening. The contact includes a pair of spaced, resilient members adapted to resiliently engage and make electrical contact with the snap connector. In one aspect of the invention, the contact is bent to define a pair of parallel spaced apart legs, one end of each of the legs being interconnected by a resilient loop portion, the other ends of the legs being free.

19 Claims, 7 Drawing Sheets

CONNECTOR FOR FETAL PROBE

This patent application is a divisional of application Ser. No. 09/237,468 filed Jan. 26, 1999, now U.S. Pat. No. 6,151,520.

BACKGROUND OF THE INVENTION

This invention relates to fetal probes and, more particularly to a connector assembly for coupling a fetal electrode to a remote monitoring device.

One type of fetal probe comprises a bipolar fetal electrode commonly used to monitor fetal heart rate during birth. This type of probe consists of a spiral fetal electrode mounted on a carrier along with an electrically isolated maternal electrode. A twisted pair of wires are connected at one end to the fetal and maternal electrodes and at their opposite ends to a connector. One such connector consists of a pair of axially spaced electrodes which are electrically isolated and each of which is connected to one of the wires. The connector is adapted to be coupled to a socket having axially spaced connectors which, in turn, are coupled by a cable to the monitor.

Initially, the twisted pair of conductors and the connector are disposed in a hollow drive tube. The end of the drive tube is inserted into the mother's cervix until the forward end contacts the fetus. The role of the drive tube is to push forwardly until the spiral fetal electrode at the forward end makes contact with the fetal epidermis. The drive tube is then rotated to screw the spiral electrode into the fetal epidermis. The drive tube is then slid over the wires and the connector while the bipolar electrodes and the twisted pair of wires remain within the mother and connected to the fetus. The removal of prior art tubes required the dexterous manipulation of the drive tube which were designed to maintain a grip on the twisted pair so as to insure that the drive tube is engaged at the distal end. Defeating the grip tended to be cumbersome. In these prior art connectors, the connector at the other end of the twisted pair of conductors is exposed. Such exposed electrodes could soil or contact energy sources and tended to be disconcerting to the patient or her partner.

In one type of assembly the socket for receiving the connector is mounted on a support or circuit board which electrically connects to a plate mounted on the mother's leg by an adhesive pad and provides a reference for the fetal and maternal electrodes. The support or circuit board connects to the leg plate by a snap electrical connector. Such snap connectors do not uniformly provide a distinct snap to indicate that good electrical contact has been achieved. In addition, the forces necessary to couple and disconnect the contacts are not consistent. As a result, medical personnel may not be aware should a good electrical connection not be achieved.

SUMMARY OF THE INVENTION

In general terms, one aspect of the invention comprises a fetal electrode assembly for use in monitoring fetal heart rate, the assembly being used in conjunction with a fetal monitor coupling device. The assembly comprises a fetal electrode and a maternal electrode mounted on an insulating holder, a connector configured to be received in an opening in the coupling device and having first and second tubular contacts separated and electrically isolated from each other and positioned to make electrical contact with complementary contact members in the coupling device, the first tubular contract having a larger diameter than the second tubular contact. An insulated pair of elongated flexible wires electrically connects a respective one of the contacts to a respective one of the fetal and maternal electrodes and an elongate tubular sheath covers the connector and is configured to be received in the open end. The sheath has a first opened end extending over and receiving the ends of the pair of flexible wires and an opposite open end spaced from each of the electrodes so that a gap is formed between the electrodes and the open end of the sheath.

Another aspect of the invention comprises the combination of a fetal electrode assembly and a fetal monitor coupling device for use in monitoring fetal heart rate. The assembly comprises a fetal electrode and a maternal electrode secured to an insulating holder, a connector configured to be received in an opening in the coupling device housing and having at least two contacts separated and electrically isolated from each other, an insulated pair of elongate flexible wires electrically connecting a respective one of the contacts to a respective one of said fetal and maternal electrodes. The coupling device includes third and fourth contacts disposed for receiving the first and second contacts, respectively, the third contact comprising a tubular member coaxial with and having one end opposed to an opening in the coupling device, and the fourth contact comprises an elongate member having one end disposed within the third contact member and electrically isolated therefrom, the other end of the fourth contact extending from the one end of the third contact and toward the opening.

According to another aspect, the invention comprises the combination of a fetal electrode assembly and a fetal monitor coupling device for use in monitoring fetal heart rate. The assembly comprises a fetal electrode and a maternal electrode mounted on an insulating holder, a connector configured to be received in an opening in the coupling device housing and having first and second contacts separated and electrically isolated from each other. Third and fourth contacts are disposed in the coupling device housing and are separated and electrically isolated from each other in an opposed relation to an opening in the housing, and positioned to make electrical contact with the first and second contacts respectively. An insulated pair of elongated flexible wires electrically connect a respective one of the first and second contact to a respective one of the fetal and maternal electrodes. The coupling device housing has a second opening for receiving a snap connector of an electrode and a fifth contact is disposed within the housing and includes a wire bent to define a pair of parallel spaced apart legs, one end of each of the legs being interconnected by a resilient loop section, the other ends of the legs being free. The legs are adapted to resiliently engage a snap connector. A support is disposed in the housing and a mounting member is engageable with a support in the housing and includes a cavity for receiving the fifth contact for mounting the fifth contact on the support, the support having conductors connected, respectively, to the third, fourth, and fifth contacts.

The invention provides a new and improved connector for bipolar electrodes which does not expose the patient to electrically energized objects. The invention also provide a new and improved clamp for the drive tube of a bipolar electrode and more particularly a quick release clamp for the drive tube of a bipolar electrode. Moreover, the invention includes a new and improved leg plate connector for bipolar electrodes which provides a more reassuring appearance to the patient and her partner and an audible or other more consistent indication that contact has been achieved.

DESCRIPTION OF THE PREFERRED EMBODIMENT

Figure 1:
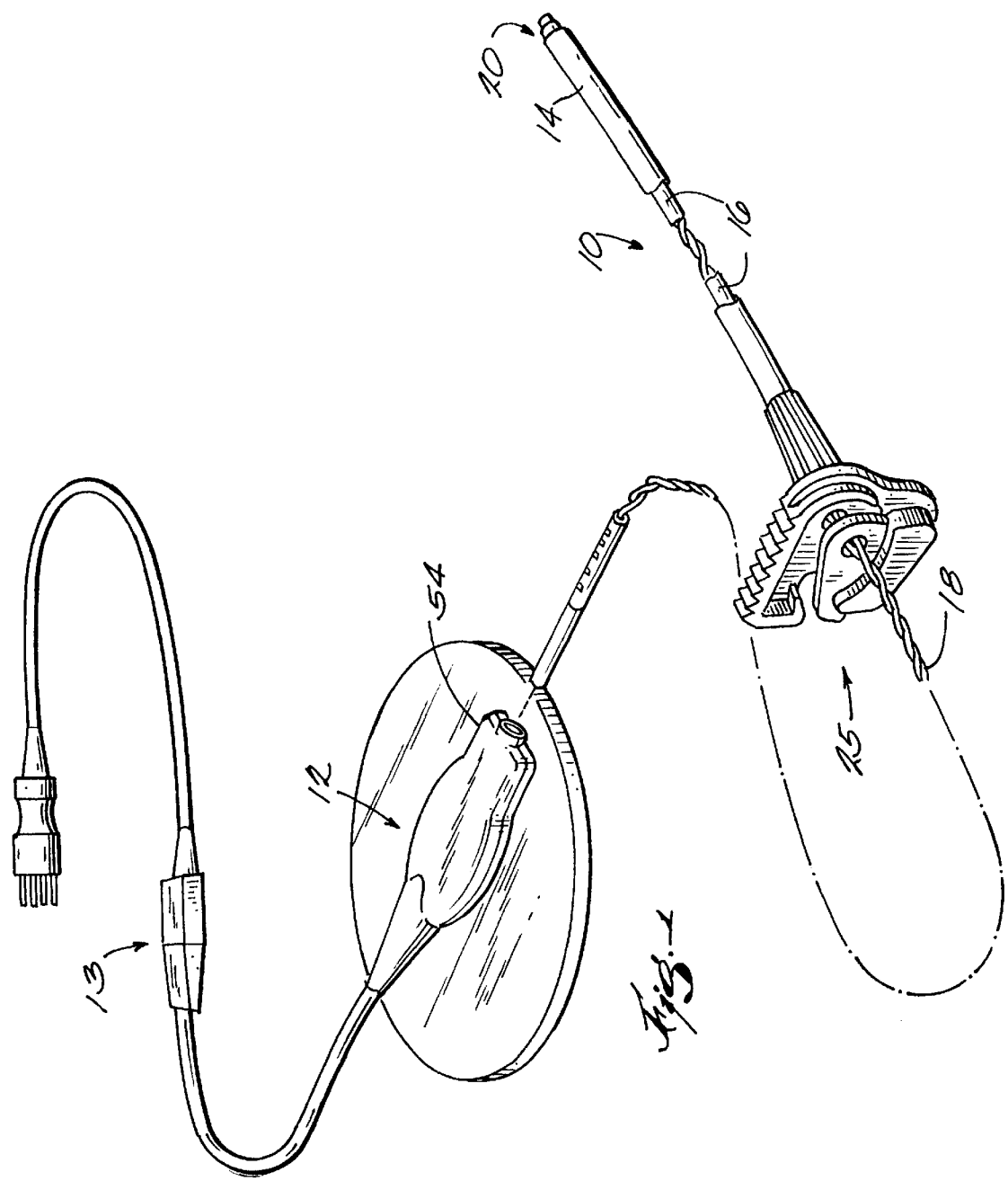
FIG. 1 is an exploded perspective view of an embodiment of a fetal electrode assembly according to the invention.
Figure 2:
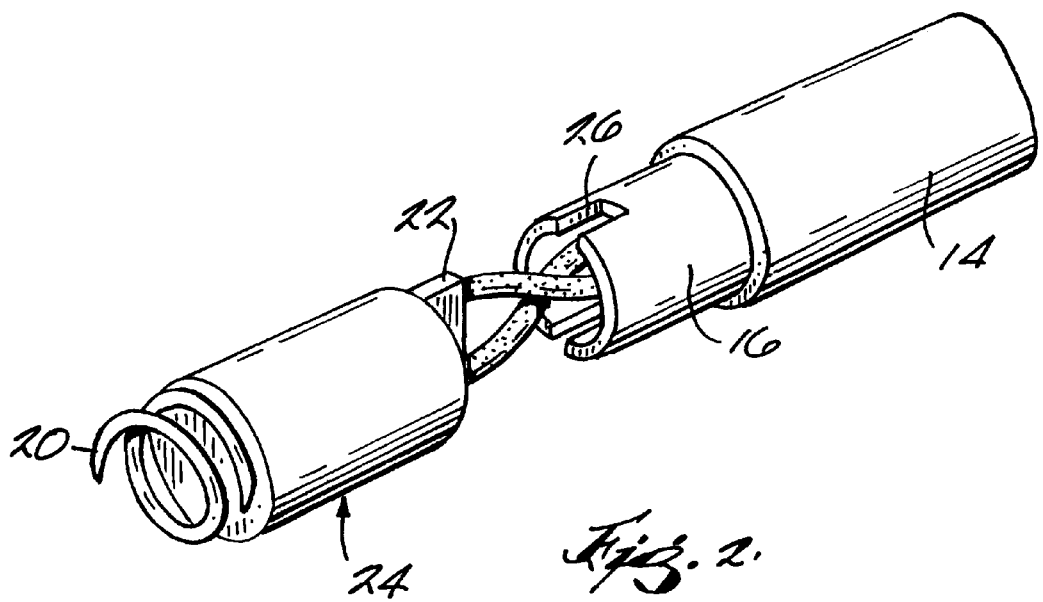
FIG. 2 is a perspective view of the forward end of a bipolar fetal electrode which forms a part of the connector assembly shown in FIG. 1.

An embodiment of a fetal electrode assembly which incorporates the invention, is shown in FIGS. 1 and 2 to include an electrode and drive assembly 10 for coupling to a fetus and the mother, a coupling assembly 12 and a cable assembly 13 for connecting the electrode assembly to a fetal monitor (not shown).

The electrode and drive assembly 10 includes a guide tube 14, a driving tube 16, and a twisted pair of wires 18, the distal ends of which are connected, respectively, to fetal and maternal electrodes 20 and 22. A nonconductive plastic holder 24 supports and electrically insulates the fetal electrode 20 from the maternal electrode 22. The guide tube 14 has a larger diameter than and is telescopingly received over the drive tube 16. At the proximal end of the drive tube 16 there is a wire clamp 25.

The fetal electrode 20, shown in FIG. 2, is in the form of a spiral electrode having a pointed end. The maternal electrode 22 is engaged by slots 26 in the forward end of the driving tube 16 so that the pointed end of the fetal electrode 20 can be rotated and be driven into the fetal epidermis by the rotation of the driving tube 16. After the spiral electrode 20 has engaged the fetus, the guide and driving tubes 14 and 16 may be pulled over a connector 28 at the proximal end of the twisted pair 18, which remain in the birth canal. For more complete description of the fetal and maternal electrodes 20 and 22 and the holder 24, reference is made to U.S. Pat. No. Re 28,990, which is incorporated by reference herein.

Figure 3:
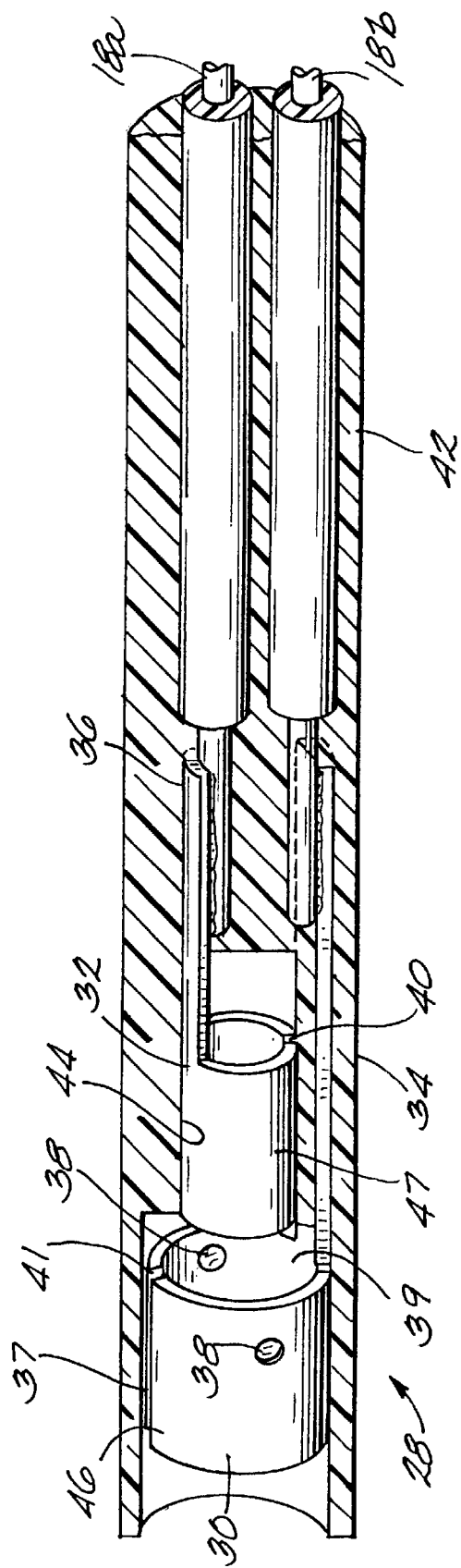
FIG. 3 is a perspective view, with parts broken away, of the connector which forms a portion of the assembly shown in FIG. 1.

FIG. 3 shows the connector 28 attached to the proximal end of the twisted pair 18 in accordance with the invention. The connector 28 comprises a generally cylindrical forward contact 30 and a coaxial rear cylindrical contact 32, each of which is formed of a suitable conductive material, such as copper, brass or nickel. Contacts 30 and 32 have an elongate, rearwardly extending tail portions 34 and 36, respectively. Each tail portion 34 and 36 has a surface for respectively receiving conductors 18a and 18b of the twisted pair 18 and to which each is connected in a suitable manner, such as by welding or soldering. The forward contact 30 has a elongate slit 37 to permit some expansion and preferably has one or more dimples 38 extending from its inner surface 39 which act as detent. A similar slit 40 is formed in the rear contact 32. A shell or sheath 41 is fixed in a surrounding relation to the contacts 30 and 32 and its rear end is overmolded at 42 to bond to the twisted pair 18. The inner surface 44 of the sheath 41 engages the outer surfaces 46 and 47, respectively, of the contacts 30 and 32 and of the tail portions 34 and 36. The forward end of the sheath 41 extends beyond the forward end of the contact 30 and a portion of the sheath 41 fills the gap between the outer surface 47 of contact 32 and the tail portion 34 of the front contact 30.

The coupling assembly 12 is shown in FIGS. 1, and 4–6 to include a housing 54, a suitable support which may take the form of a circuit board 56, a coaxial plug 57, a snap spring contact 58 and a mounting member 59. The housing 54 is preferably molded of upper and lower portions 54a and 54b which are suitably joined to enclose the circuit board 56 and the various components mounted thereon. The coupling assembly 12 cooperatively engages a conventional or specific electrode 60 adapted to be mounted, for example, on the skin of the mother. In particular, the snap spring 58 is formed of a resilient conductive metallic material and includes a pair of parallel spaced legs or members 61. One end of each leg 61 is free and the opposite ends are interconnected by a resilient loop 62. The legs 61 are adapted to resiliently engage the snap connector 63 of the electrode 60. The snap spring 58 also has a coupling loop or members 64 which is received in an opening 65 in circuit board 56 for electrically and mechanically connecting the spring 58 to the circuit board. The spring 58 performs the dual functions of securing the connector 63 and providing an electrical connection thereto.

The spring 58 is received within a recess 66 formed in the lower surface of member 59. The mounting member 59 includes a plurality of indexing legs 67 which are receivable in holes 68 in circuit board 54 in surrounding relation to an opening 69 for receiving the snap contact 63 of electrode 60. After the spring contact 58 has been positioned in the recess 66a to provide the desired spring contact, the legs 67 are inserted into holes 68 and the coupling loop 64 is inserted into opening 65. This prevents relative movement between the spring contact 58 and the mounting member 59. In addition, a small pair of legs 65a are provided in the recess 65 and straddle the legs 61 to impede the spread of the free end of legs 61. This adapts the apparent resiliency and thus the engagement force of the shape of contact 63.

Figure 4:
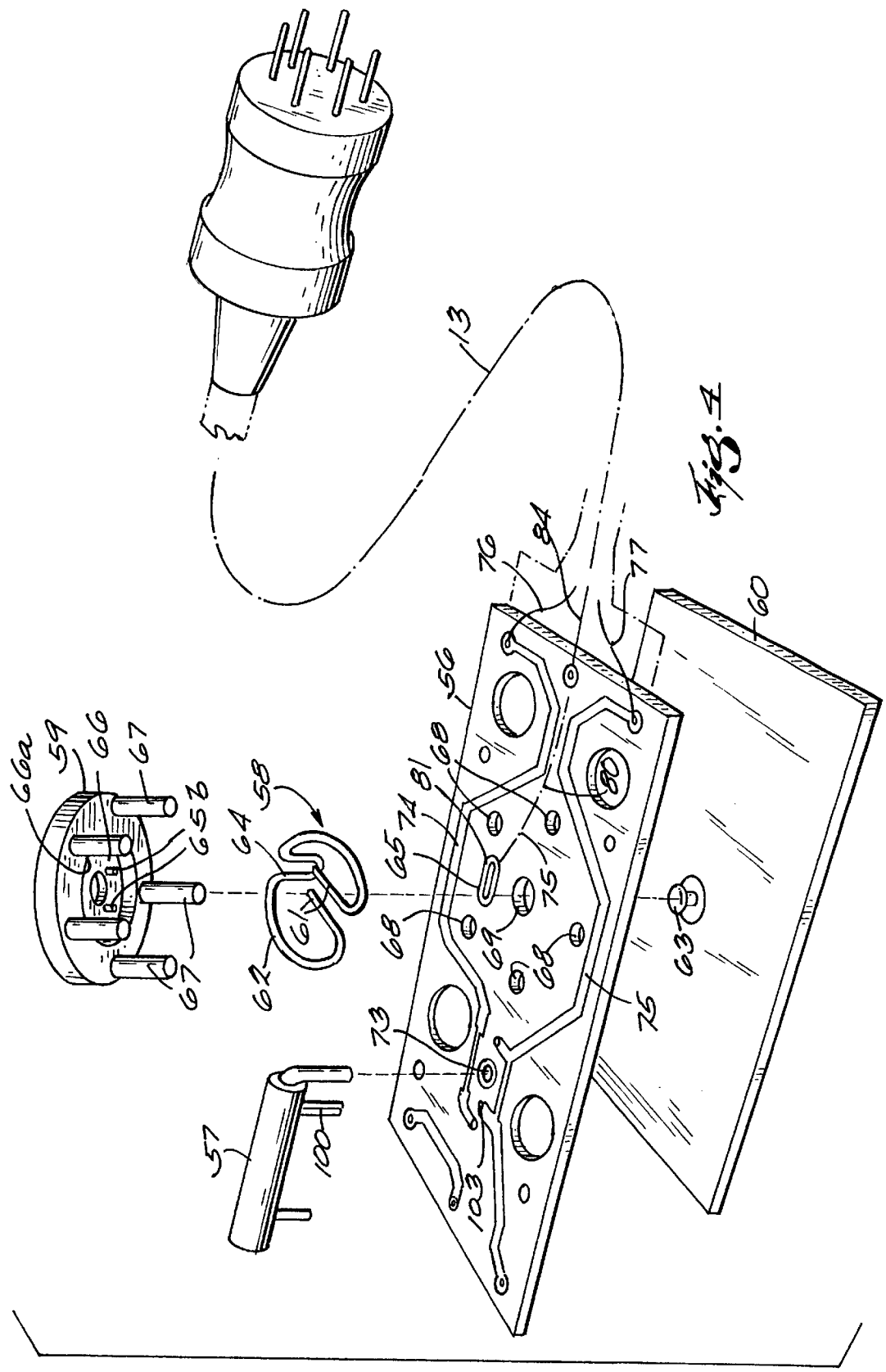
FIG. 4 is an exploded perspective view of the fetal monitoring coupling assembly used with the connector assembly shown in FIG. 1.
Figure 5:
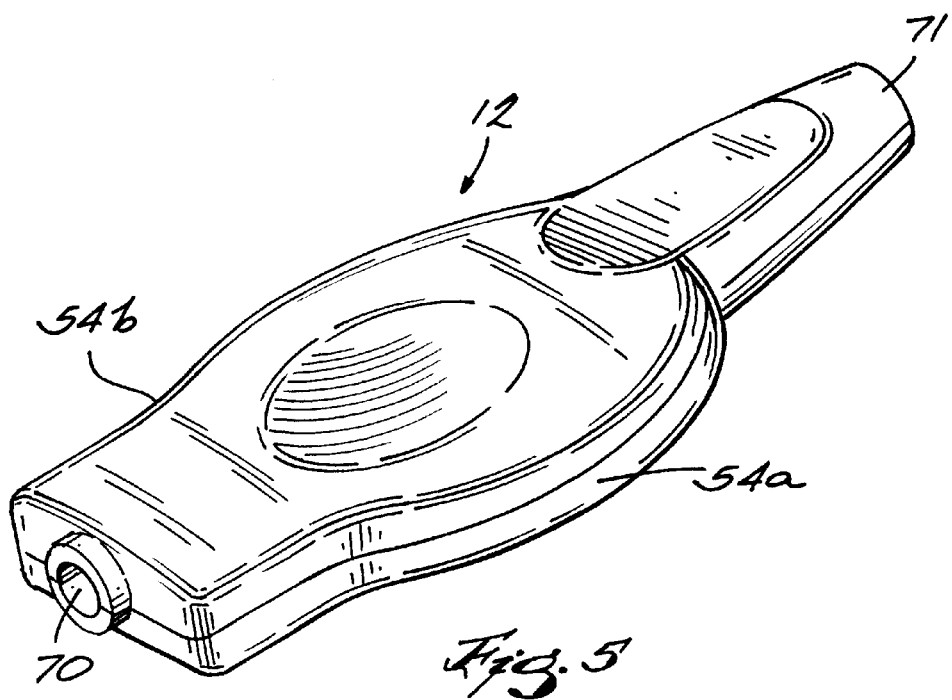
FIGS. 5 and 6 are top and bottom perspective views, respectively, of the coupling assembly of FIG. 4.
Figure 6:
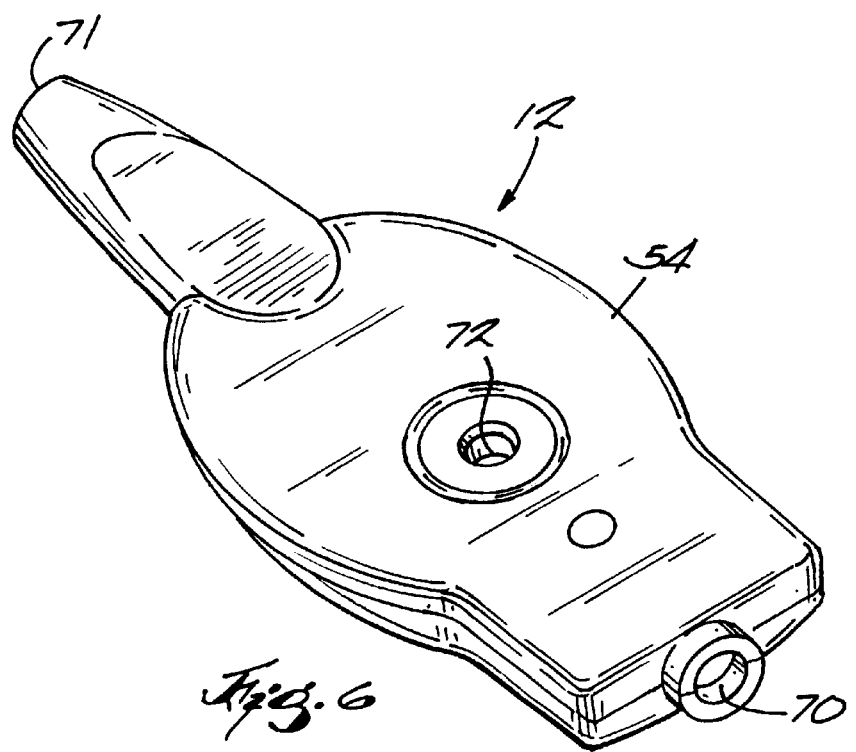

While the spring 58 and the mounting member 59 are shown in FIG. 4 above the circuit board 56, in actual practice, it may be disposed above or below the circuit board. In addition, while member 59 is shown to be a separate piece, it may be formed as an integral part of the upper or lower housing portions 54a or 54b.

The housing 54 is formed of any suitable moldable insulating material for encapsulating the circuit board 56, the plug 57, the spring contact 58 and the mounting member 59. A first opening 70 in the front of housing 54 communicates with the plug 57, a second opening 71 at the rear of the housing 54 receives cable 13, and a third opening 72 in the bottom of housing 54 communicates with the spring contact 58.

Circuit board 54 is formed of a suitable, semi-rigid, insulating material and includes an opening 73 adjacent its forward end for receiving the plug 57. Conductive strips 74 and 75 are provided on circuit board 54 and are, respectively, connected at one end to third and fourth contacts within the plug 57 and at their other ends do the conductors 76 and 77 which form a part of the cable 13. In addition, a conductive strip 80 on the opposite side of circuit board 57 is connected at one end to snap a contact 81 surrounding opening 65 for engagement with spring contact 58. The other end of strip 80 is connected to conductor 84 which also forms a part of the cable 13.

Figure 7:
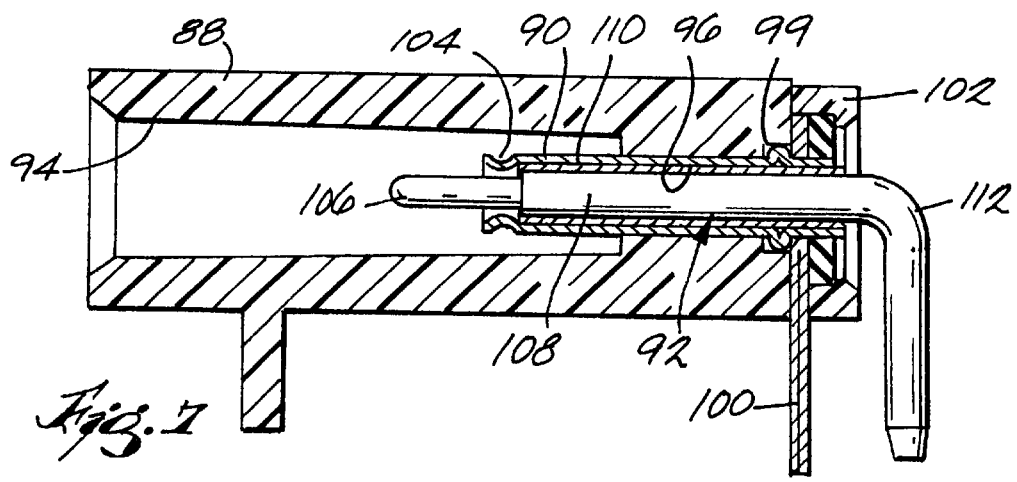
FIG. 7 is a cross-sectional view of a plug connector which forms a portion of the assembly of FIG. 1.

The plug 57 is shown more particularly in FIG. 7 to include an outer tubular shell 88, a first coaxial contact 90 and a second coaxial contact 92. The outer shell 88 has a cylindrical central bore 94 sized for receiving the sheath 41 of connector 28 with a sliding fit. The first contact 90 consists of a generally tubular conductive member which is received in a counter bore 96 in the end of shell 88. A bead 98 is formed adjacent the fixed end of contact 90 for engaging a complimentary hole formed in an elongate, downwardly extending conductive member 100 that is held in position by an end cap 102. Conductive member 100 is received in an opening 103 in circuit board 56 and is electrically connected to conductive strip 75.

The outer diameter of the free end of contact 90 is sized to receive the inner surface 39 of the forward contact 30 of connector 28. A groove 104 is formed in the forward end of contact 90 and that portion of the contact is unsupported to permit the contact to flex for receiving the detents 38 formed on the contact 30.

The second contact 92 comprises a rod-like member formed of a suitable conducting material. The forward end 106 of contact 92 has a diameter sized to telescopingly receive the contact 32. A larger diameter portion 108 of contact 92 is received within the tubular contact 90 and is separated therefrom by a sleeve of electrically insulating material 110. The portion 108 extends through an opening 112 formed in the end cap 102 and downwardly therefrom into opening 73 in the circuit board 56 and is electrically connective to the conductive strip 74.

Figure 9:
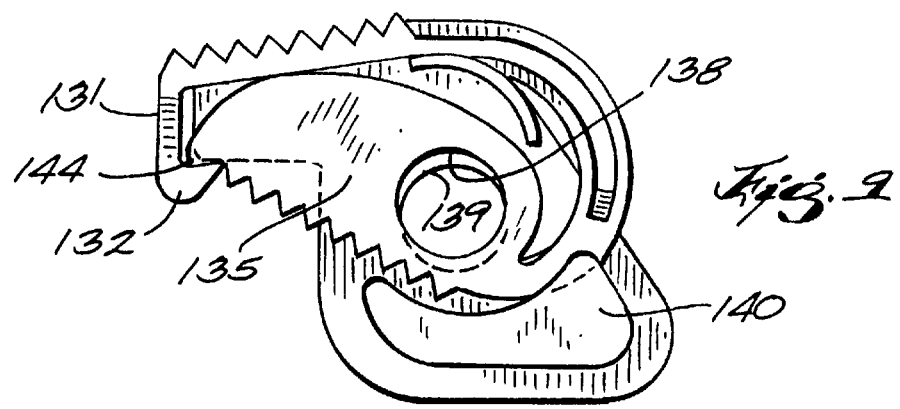
FIGS. 9 and 10 show the latch of FIG. 7 in its latching and unlatching modes.
Figure 10:
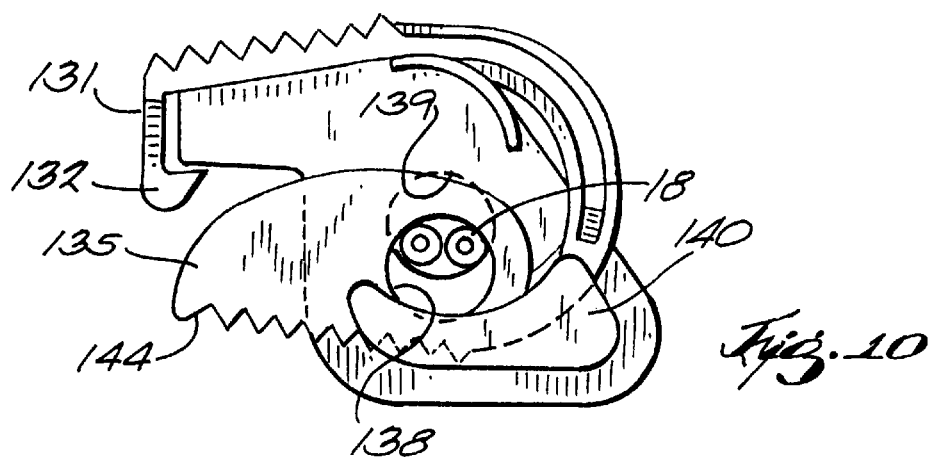
Figure 8:
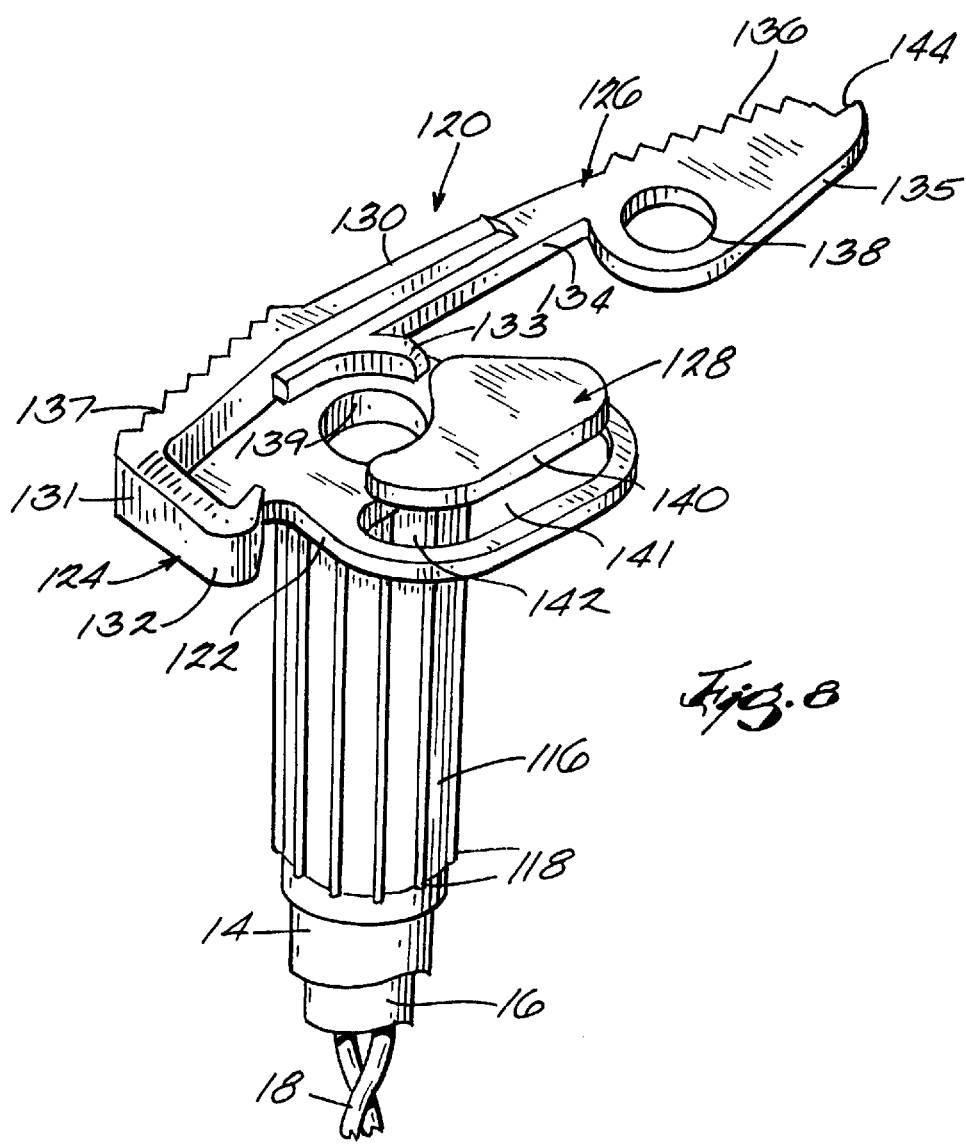
FIG. 8 is a perspective view a clamp which forms a portion of the assembly of FIG. 1.

The clamp 25 is preferably formed of a plastic material and is shown in FIG. 8 in its free molded form and in FIGS. 9 and 10 in its operative mode as will be described more fully below. Clamp 25 includes a hollow tubular neck portion 116 which is fixed at one end to the drive tube 16 and a clamping portion 120 fixed to the opposite end of neck portion 116. The outer surface of the neck portion 116 may have a plurality of longitudinal flutes 118 to facilitate gripping.

The clamping portion 120 includes a planer base 122, a front latch 124, a clamp 126 and a retainer 128.

A side wall 130 is formed along one side of the base 122 and extends upwardly therefrom. Latch 124 includes an arm 131 attached at one end to the forward end of sidewall 130 and in parallel with the front of the base 122. A hook 132 is formed at the free end of arm 131.

At the rear of the base 122 and between the side wall 130 and the retainer 128 is an arcuate nesting wall 133.

The clamp 126 includes an arm 134 extending rearwardly from the side wall 130 and a clamp member 135 formed at the free end of arm 134. The outer side of the clamp member 135 is serrated at 136 to form a non-slip finger engaging surface. The outer surface of the side wall 130 is also serrated at 137 for the same purpose. A hole 138 is formed in the clamp member 135 for receiving the twisted pair 18 as will be discussed more fully below. There is also a similarly sized hole 139 in the base 122 which communicates with the interior of the neck portion 116 and the drive tube 16.

The retainer 128 includes an upper plate 140 supported by a side wall 141 in a parallel spaced apart relation above the base 122. The forward end of the it plate 140 extends beyond that of the wall 141 to define a gap 142.

In operation, the arm 134 is bent inwardly and flexed slightly upwardly to permit the clamp member 135 to pass around the inner edge of the plate 140 and down into the space between the plate 140 and the base 122 as the arm 134 flexes about the nesting wall 133. As the clamp member 135 moves inwardly, it engages the hook 132. This causes the arm 131 to flex outwardly until a catch 144 on clamp 135 is positioned as shown in FIG. 9, after which the arm 130 returns to its position shown in FIG. 9 to latch the clamp member 135 in this position. The twisted pair 18 may then be inserted into the drive tube 116 through holes 138 and 139 after which the clamping member 135 is released from hook 132. This clamps the twisted pair 18 between the edges of the holes 138 and 139 and against movement relative to the drive tube 16 as shown in FIG. 10.

After the twisted pair 18 has been secured, the fetal electrode 20 is positioned in the mother as discussed in U.S. Pat. No. Re 28,990, after which the guide tube 16 and the guide tube 14 are removed. The connector 28 is then inserted into the coaxial plug 57 and the snap spring contact 58 is coupled to the electrode 60 which may then be attached to the mother's leg. Because the contacts 30 and 32 of connector 28 and 90 and 92 of plug 57 are circular in cross section, the connection can be made without the necessity of orienting the connector 28.

Figure 11:
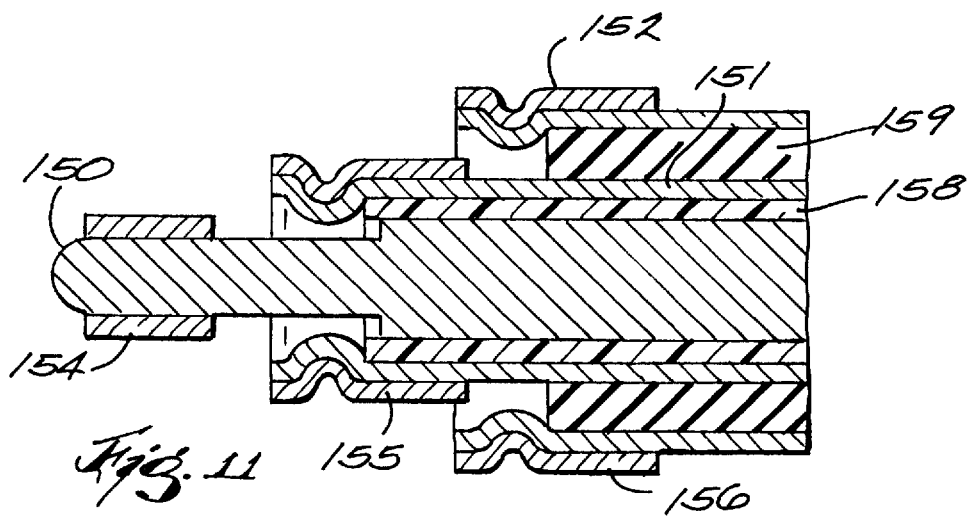
FIG. 11 shows an alternate embodiment of the invention.

While a bipolar connector is shown in FIGS. 3 and 7, the connector and plug may include three or more conductive paths as shown in FIG. 11. Here, the plug includes first, second and third coaxial contacts 150, 151, and 152 and the connector includes cylindrical, coaxial, axially spaced contacts 154, 155 and 156. Insulating sleeves 158 and 159 electrically isolate contacts 150, 151 and 152.

While only a few embodiments of the invention has been illustrated and described, it is not intended to be limited thereby but only by the scope of the appended claims.

I claim:

1. A coupling assembly for a fetal scalp electrode used in monitoring fetal heart rate, the coupling assembly comprising:

a first housing portion;

a second housing portion having an opening for receiving a snap connector of an electrode mounted on a patient's body;

a circuit board between the first and second housing portions; and a contact coupled to the circuit board and including a resilient member adapted to resiliently engage and make electrical contact with the snap connector;

wherein the circuit board includes an opening, and wherein the contact includes a coupling member received in the opening of the circuit board for electrically and mechanically coupling the contact to the circuit board; and wherein the circuit board includes a second opening substantially aligned with the opening in the second housing portion for receiving at least a portion of the snap connector.

2. The coupling assembly of claim 1, wherein the contact further includes a second resilient member cooperating with the first resilient member to resiliently engage and make electrical contact with the snap connector, the first and second resilient members being generally parallel.

3. The coupling assembly of claim 1, wherein the contact includes a wire bent to define a pair of parallel resilient members, one end of each of the resilient members being interconnected by a resilient loop portion, the other end of each of the resilient members being free.

4. The coupling assembly of claim 1, wherein the contact is mounted between the circuit board and the first housing portion.

5. The coupling assembly of claim 1, further comprising:
a mounting member coupled to the circuit board and having a recess for receiving the contact.

6. A coupling assembly for a fetal scalp electrode used in monitoring fetal heart rate, the coupling assembly comprising:
a first housing portion;
a second housing portion having an opening for receiving a snap connector of an electrode mounted on a patient's body;
a circuit board between the first and second housing portions;
a contact coupled to the circuit board and including a resilient member adapted to resiliently engage and make electrical contact with the snap connector; and
a mounting member coupled to the circuit board and having a recess for receiving the contact;
wherein the circuit board includes a plurality of mounting openings, and the mounting member includes a plurality of legs received in the respective mounting openings for mounting the mounting member on the circuit board.

7. The coupling assembly of claim 6, wherein the contact further includes a second resilient member cooperating with the first resilient member to resiliently engage and make electrical contact with the snap connector, the first and second resilient members being generally parallel.

8. The coupling assembly of claim 6, wherein the contact includes a wire bent to define a pair of parallel resilient members, one end of each of the resilient members being inter connected by a resilient loop portion, the other end of each of the resilient members being free.

9. The coupling assembly of claim 6, wherein the circuit board includes an additional opening substantially aligned with the opening in the second housing portion for receiving at least a portion of the snap connector.

10. The coupling assembly of claim 6, wherein the contact is mounted between the circuit board and the first housing portion.

11. The coupling assembly of claim 6, wherein the circuit board includes an additional opening, and wherein the contact includes a coupling member received in the additional opening of the circuit board for electrically and mechanically coupling the contact to the circuit board.

12. The coupling assembly of claim 6, wherein the mounting member includes a leg in the recess for impeding the movement of the resilient member.

13. A coupling assembly for a fetal scalp electrode used in monitoring fetal heart rate, the coupling assembly comprising:
a first housing portion;
a second housing portion having an opening for receiving a snap connector of an electrode mounted on a patient's body;
a circuit board between the first and second housing portions;
a contact coupled to the circuit board and including a resilient member adapted to resiliently engage and make electrical contact with the snap connector; and
a mounting member coupled to the circuit board and having a recess for receiving the contact;
wherein the mounting member includes a leg in the recess for impeding the movement of the resilient member.

14. The coupling assembly of claim 13, wherein the contact further includes a second resilient member cooperating with the first resilient member to resiliently engage and make electrical contact with the snap connector, the first and second resilient members being generally parallel.

15. The coupling assembly of claim 13, wherein the contact includes a wire bent to define a pair of parallel resilient members, one end of each of the resilient members being interconnected by a resilient loop portion, the other end of each of the resilient members being free.

16. The coupling assembly of claim 13, wherein the circuit board includes an opening substantially aligned with the opening in the second housing portion for receiving at least a portion of the snap connector.

17. The coupling assembly of claim 13, wherein the contact is mounted between the circuit board and the first housing portion.

18. The coupling assembly of claim 13, wherein the circuit board includes an opening, and wherein the contact includes a coupling member received in the opening of the circuit board for electrically and mechanically coupling the contact to the circuit board.

19. The coupling assembly of claim 13, wherein the circuit board includes a plurality of mounting openings, and the mounting member includes a plurality of legs received in the respective mounting openings for mounting the mounting member on the circuit board.

* * * * *